US008204288B2

(12) United States Patent
Kim et al.

(10) Patent No.: US 8,204,288 B2
(45) Date of Patent: *Jun. 19, 2012

(54) APPARATUS AND METHOD FOR PROCESSING AN ULTRASOUND SPECTRUM IMAGE

(75) Inventors: Hye Jung Kim, Gimpo-si (KR); Ki Jong Lee, Yongin-si (KR); Sung Ho Kim, Seoul (KR); Eun Ho Yang, Seoul (KR); Cheol An Kim, Yongin-si (KR)

(73) Assignee: Medison Co., Ltd., Hongchun-gun (KR)

( * ) Notice: Subject to any disclaimer, the term of this patent is extended or adjusted under 35 U.S.C. 154(b) by 0 days.

This patent is subject to a terminal disclaimer.

(21) Appl. No.: 12/948,487

(22) Filed: Nov. 17, 2010

(65) Prior Publication Data

US 2011/0063945 A1    Mar. 17, 2011

Related U.S. Application Data

(63) Continuation of application No. 11/413,157, filed on Apr. 28, 2006, now Pat. No. 7,864,998.

(30) Foreign Application Priority Data

May 26, 2005   (KR) .................. 10-2005-0044360

(51) Int. Cl.
*G06K 9/00* (2006.01)
(52) U.S. Cl. ......... 382/128; 382/129; 382/131; 382/132
(58) Field of Classification Search .................. 382/128, 382/130, 131; 600/454, 473, 468, 455, 504, 600/453, 447; 702/76; 375/200–342
See application file for complete search history.

(56) References Cited

U.S. PATENT DOCUMENTS

| 5,582,176 | A | | 12/1996 | Swerling et al. |
| 5,647,366 | A | | 7/1997 | Weng |
| 5,868,676 | A | * | 2/1999 | McCabe et al. ............... 600/454 |
| 6,050,948 | A | * | 4/2000 | Sasaki et al. .................. 600/453 |
| 6,577,967 | B2 | | 6/2003 | Mo et al. |

(Continued)

OTHER PUBLICATIONS

T. D'Alessio, "'Objective' algorithm for maximum frequency estimation in Doppler spectral analysers", Medical and Biological Engineering & Computing, vol. 23, Jan. 1985, pp. 63-68, XP008068800.

*Primary Examiner* — Vikkram Bali
*Assistant Examiner* — Nancy Bitar
(74) *Attorney, Agent, or Firm* — Oblon, Spivak, McClelland, Maier & Neustadt, L.L.P.

(57) ABSTRACT

There is provided a method of processing an ultrasound spectrum image. According to such method, a spectrum image is formed based on ultrasound data and then the noise is removed from the spectrum image. The noise-removed spectrum image is matched with one or more spectrum models representing specific spectrum types. Then, whether or not the noise-removed spectrum image contains an aliasing is checked. If the noise-removed spectrum image contains the aliasing, then the aliasing is removed from the noise-removed spectrum image to provide a noise-removed spectrum image without the aliasing. Thereafter, contour tracing is performed on the noise-removed spectrum image without the aliasing to detect contour points. Further, peak tracing is performed on the noise-removed spectrum image without the aliasing to detect peaks.

8 Claims, 18 Drawing Sheets

U.S. PATENT DOCUMENTS

| | | |
|---|---|---|
| 6,663,566 B2 | 12/2003 | Pan et al. |
| 6,733,454 B1 | 5/2004 | Bakircioglu et al. |
| 7,682,311 B2 * | 3/2010 | Simopoulos et al. ......... 600/454 |
| 7,864,998 B2 * | 1/2011 | Kim et al. .................... 382/128 |
| 2002/0019590 A1 | 2/2002 | Bang et al. |
| 2002/0116141 A1 * | 8/2002 | Mo et al. ......................... 702/76 |
| 2003/0045797 A1 | 3/2003 | Christopher et al. |
| 2003/0158484 A1 | 8/2003 | Pan et al. |

* cited by examiner

APPARATUS AND METHOD FOR PROCESSING AN ULTRASOUND SPECTRUM IMAGE

CROSS-REFERENCE TO RELATED APPLICATIONS

This application is a continuation of U.S. application Ser. No. 11/413,157, filed Apr. 28, 2006, the entire content of which is incorporated herein by reference. U.S. application Ser. No. 11/413,157 is based upon and claims priority under 35 U.S.C. 119 to Korean Application No. 10-2005-044360, filed May 26, 2005.

FIELD OF THE INVENTION

The present invention generally relates to ultrasound diagnostic systems, and more particularly to an ultrasound diagnostic system for processing an ultrasound spectrum image and a method of implementing the same.

BACKGROUND OF THE INVENTION

An ultrasound diagnostic system is now widely used to inspect the internal condition of a human body. The ultrasound diagnostic system may obtain an image of the single layer or blood flow of a soft tissue without using an invasive needle. This is typically performed through the process of radiating an ultrasound signal from the body surface of a target object to be diagnosed to a desired portion in the body, receiving the reflected ultrasound signal, and processing the received ultrasound signal (ultrasound echo signal). Compared to other medical imaging systems (e.g., X-ray diagnostic system, X-ray Computerized Tomography (CT) scanner, Magnetic Resonance Imaging (MRI) system, nuclear medicine diagnostic system, etc.), the ultrasound diagnostic system is relatively small in size and inexpensive. The ultrasound diagnostic system is further capable of displaying images in real-time and is highly safe from exposure to X-ray radiation or the like. Due to such advantages, the ultrasound diagnostic system is widely employed to diagnose the heart, abdomen and urinary organs, especially in the fields of obstetrics, gynecology and the like.

In a conventional ultrasound diagnostic system, transducers transmit ultrasound signals to a target object and receive signals reflected by the target object (echo signals). The echo signals show different patterns depending on whether the target object is stationary or moving. When the target object is moving toward the transducers, received signals have higher frequencies than when the target object is stationary. On the other hand, when the target object is moving away from the transducers, received signals have lower frequencies than when the target object is stationary. As such, the echo signals reflected by the moving target object are subject to the Doppler shift phenomenon. Due to the Doppler shift, the ultrasound diagnostic system can obtain velocity information that can be displayed on a display device. Further, the ultrasound diagnostic system can offer the velocity measurement of a blood flow based on the obtained velocity information.

Generally, contour tracing is required to detect the contour (sometimes referred to as a 'trace line') of a spectrum image. However, even when the spectrum image has aliasing, the conventional ultrasound diagnostic system does not consider the magnitude and direction of the aliasing when performing contour tracing. For this reason, the conventional ultrasound diagnostic system is disadvantageous since it cannot perform accurate contour tracing, as shown in FIG. 1. Therefore, the conventional ultrasound diagnostic system cannot provide accurate peak tracing.

Further, as the pulse wave (PW) gain for a spectrum image increases, the noise also tends to increase. Also, the noise varies for each spectrum image. However, when the conventional ultrasound diagnostic system performs the contour tracing on a spectrum image with increased noise, it determines a threshold for removing the noise based on the PW gain without analyzing the noise. Thus, since the noise varies depending on external environments (e.g., gel existence, probe type, etc.), the conventional ultrasound diagnostic system is disadvantageous in that it cannot perform accurate contour tracing, as shown in FIG. 2. Therefore, the conventional ultrasound diagnostic system cannot provide accurate peak tracing.

SUMMARY OF THE INVENTION

It is, therefore, an object of the present invention to address and resolve the above-mentioned deficiencies of the prior art. In this regard, the object of the present invention is to provide an apparatus and method for processing an ultrasound spectrum image, which can accurately perform both contour tracing and peak tracing by removing the noise from a noise-containing spectrum image and removing aliasing from an aliasing-containing spectrum image through automatically shifting the baseline.

According to one aspect of the present invention, there is provided a method of processing an ultrasound spectrum image, which comprises the following steps: (a) forming a spectrum image based on ultrasound data; (b) removing noise from the spectrum image to provide a noise-removed spectrum image; (c) matching the noise-removed spectrum image with one or more spectrum models representing specific spectrum types to check whether the noise-removed spectrum image contains an aliasing or not; (d) if it is determined that the noise-removed spectrum image contains the aliasing, removing the aliasing from the noise-removed spectrum image to provide a noise-removed spectrum image without the aliasing; (e) performing contour tracing on the noise-removed spectrum image without the aliasing to detect contour points; and (f) performing peak tracing on the noise-removed spectrum image without the aliasing to detect peaks.

According to another aspect of the present invention, there is provided a method of processing an ultrasound spectrum image, which comprises the following steps: forming a spectrum image based on ultrasound data; dividing the spectrum image into a number of sections; for each of the sections, calculating an average intensity of pixels in the section; comparing the average intensities calculated for the sections to select a section having a smallest average intensity; analyzing a histogram of the section having the smallest average intensity to detect a maximum intensity in the histogram; determining the detected maximum intensity as a threshold for removing noise from the spectrum image; and removing the noise from the spectrum image based on the determined threshold.

According to yet another aspect of the present invention, there is provided a method of processing an ultrasound spectrum image, which comprises the following steps: forming a spectrum image based on ultrasound data; analyzing the spectrum image; detecting a direction and a magnitude of an aliasing, if exists, by using one or more spectrum models representing specific spectrum types; and shifting a baseline of the spectrum image based on the detected direction and magnitude of the aliasing to remove the aliasing.

According to yet another aspect of the present invention, there is provided a method of processing an ultrasound spectrum image, which comprises the following steps: (a) forming a spectrum image based on ultrasound data; (b) checking whether a peak tracing for detecting peaks in the spectrum image is 1-peak tracing or 2-peak tracing; (c) if it is determined that the peak tracing is the 1-peak tracing, performing the 1-peak tracing on the spectrum image; and (d) if it is determined that the peak tracing is the 2-peak tracing, performing the 2-peak tracing on the spectrum image.

According to still yet another aspect of the present invention, there is provided an ultrasound diagnostic system, which comprises the following: means for forming a spectrum image based on ultrasound data; means for removing a noise from the spectrum image to provide a noise-removed spectrum image; means for matching the noise-removed spectrum image with one or more spectrum models representing specific spectrum types to check whether the noise-removed spectrum image contains an aliasing or not; if it is determined that the noise-removed spectrum image contains the aliasing, means for removing the aliasing from the noise-removed spectrum image to provide a noise-removed spectrum image without the aliasing; means for performing a contour tracing on the noise-removed spectrum image without the aliasing to detect contour points; and means for performing a peak tracing on the noise-removed spectrum image without the aliasing to detect peaks.

BRIEF DESCRIPTION OF THE DRAWINGS

The above and other objects and features of the present invention will become apparent from the following descriptions of preferred embodiments given in conjunction with the accompanying drawings, in which.

DETAILED DESCRIPTION OF THE PRESENT INVENTION

The preferred embodiments of the present invention will be described below with reference to FIGS. 3 to 22.

Figure 1:
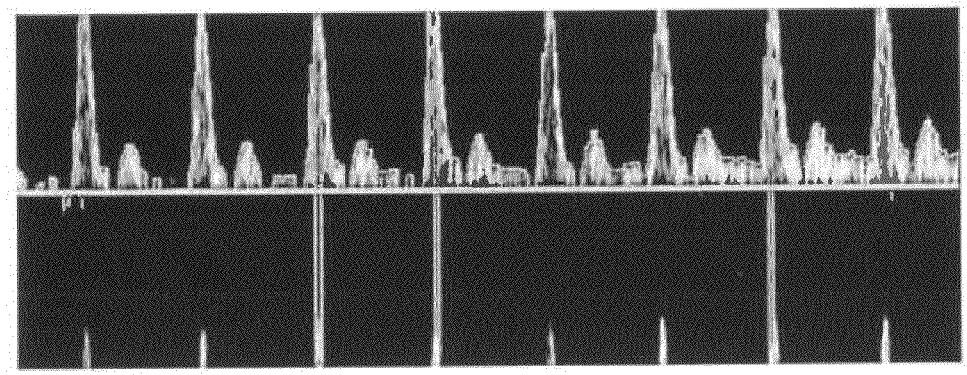
FIG. 1 shows the result of contour tracing for an aliasing-containing spectrum image in a conventional ultrasound diagnostic system.
Figure 2:
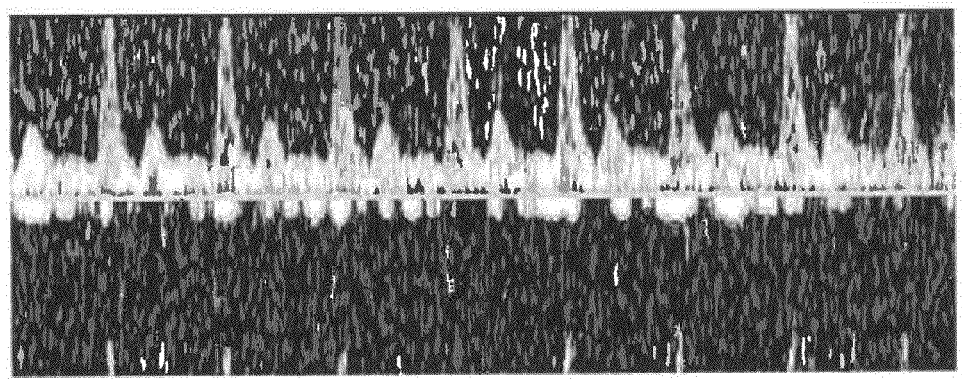
FIG. 2 shows the result of contour tracing for a spectrum image with increased pulse wave (PW) gain in a conventional ultrasound diagnostic system.
Figure 3:
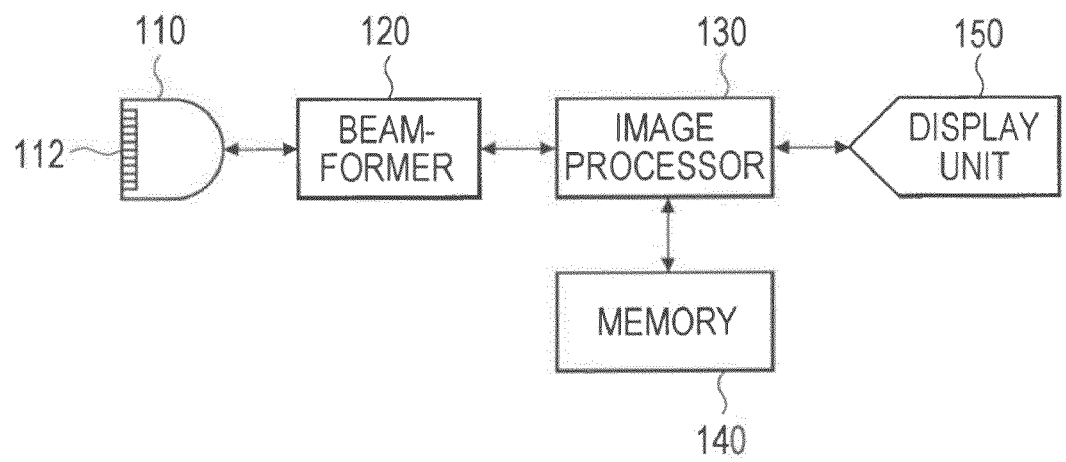
FIG. 3 is a schematic block diagram illustrating an ultrasound diagnostic system constructed in accordance with one embodiment of the present invention.

Referring now to FIG. 3, an ultrasound diagnostic system 100, which is constructed in accordance with the present invention, generally includes a probe 110, a beam-former 120, an image processor 130, a memory 140 and a display unit 150.

The probe 110 preferably includes a one-dimensional (1D) or two-dimensional (2D) array of transducers 112. The probe 110 is configured to transmit ultrasound signals to a target object and receive ultrasound echo signals. The beam-former 120 controls the transmission and reception of the probe 110. Further, in order to form a coherent beam of the echo signals from the target object, the beam-former 120 processes the received ultrasound echo signals. The image processor 130 produces spectrum signals based on the ultrasound echo signals and produces a noise-removed spectrum image based on the spectrum signals, wherein a frequency component at a specific time and velocity is represented by a shade of gray. The image processor 130 then performs contour tracing and peak tracing on the produced spectrum image to thereby provide a processed spectrum image. The processed spectrum image, which is provided by the image processor 130, is stored in the memory 140 and/or is displayed on the display unit 150. Alternatively, the memory 140 may store the raw spectrum signals instead of the resulting spectrum image.

The image processor 130, which is constructed in accordance with the present invention, will be described below in detail with reference to FIGS. 4 to 22.

Figure 4:
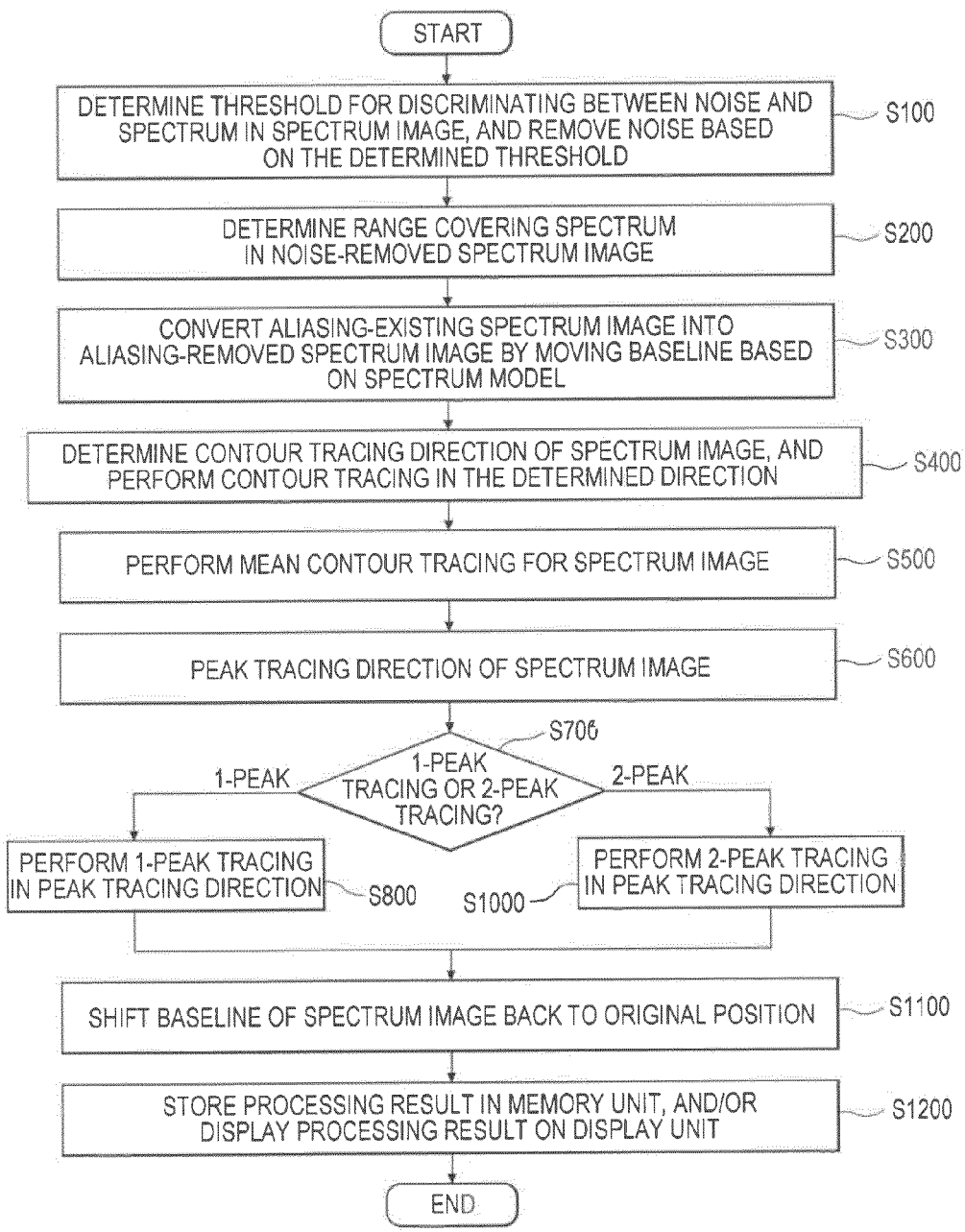
FIG. 4 is a flowchart showing the operations of an image processor included in the ultrasound diagnostic system shown in FIG. 3.

FIG. 4 is a flowchart showing the operations of the image processor 130. The image processor 130 determines a threshold for discriminating between a noise and a spectrum in a spectrum image. It then removes the noise based on the determined threshold (S100). Step S100 will be described in more detail in view of FIGS. 5, 6A and 6B.

Figure 5:
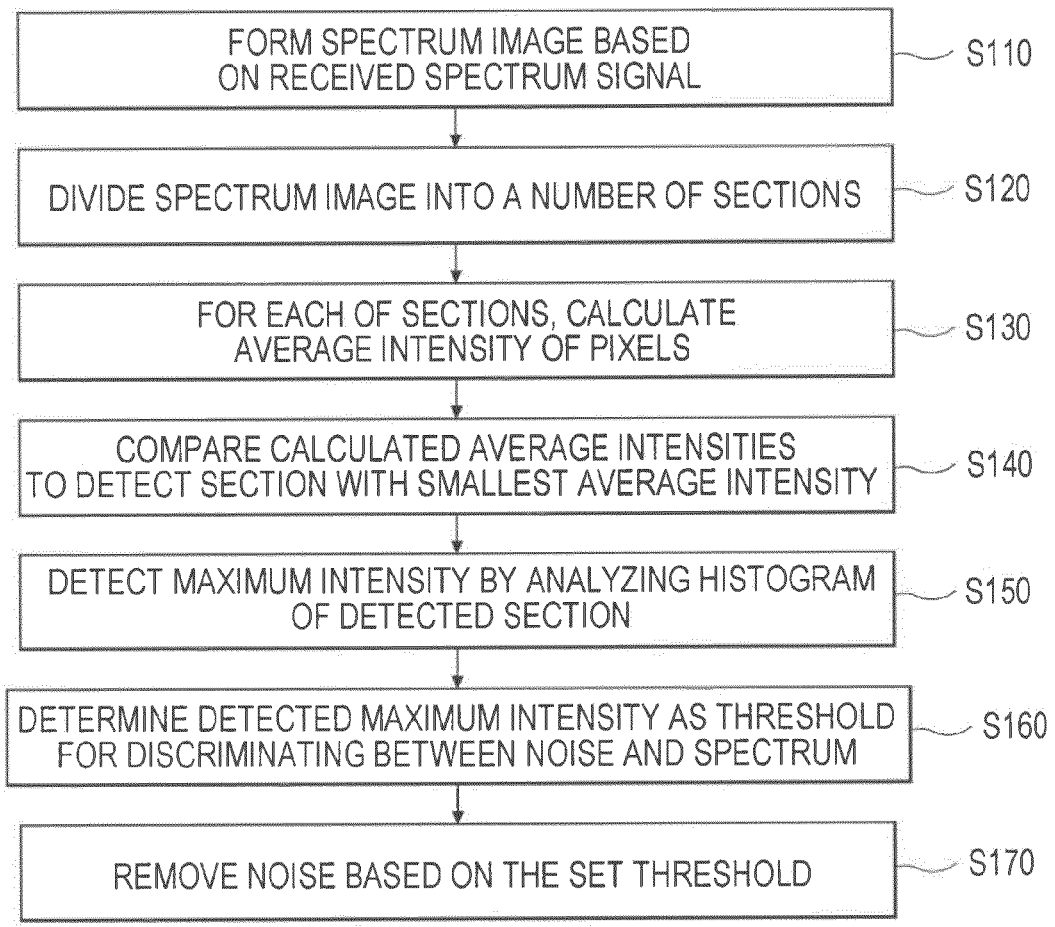
FIG. 5 is a flowchart showing the process of determining a threshold for discriminating between a noise and a spectrum in a spectrum image and removing the noise from the spectrum image based on the determined threshold.
Figure 6A:
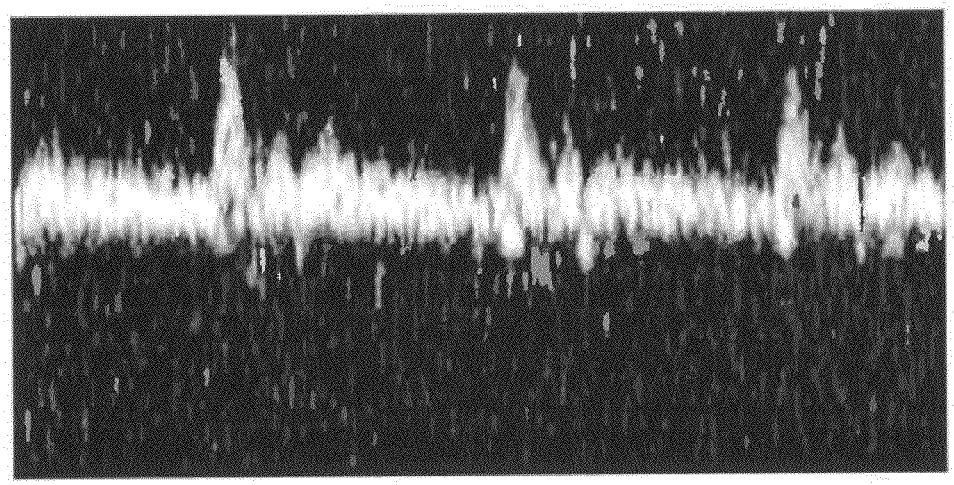
FIG. 6A shows a noise-containing spectrum image.
Figure 6B:
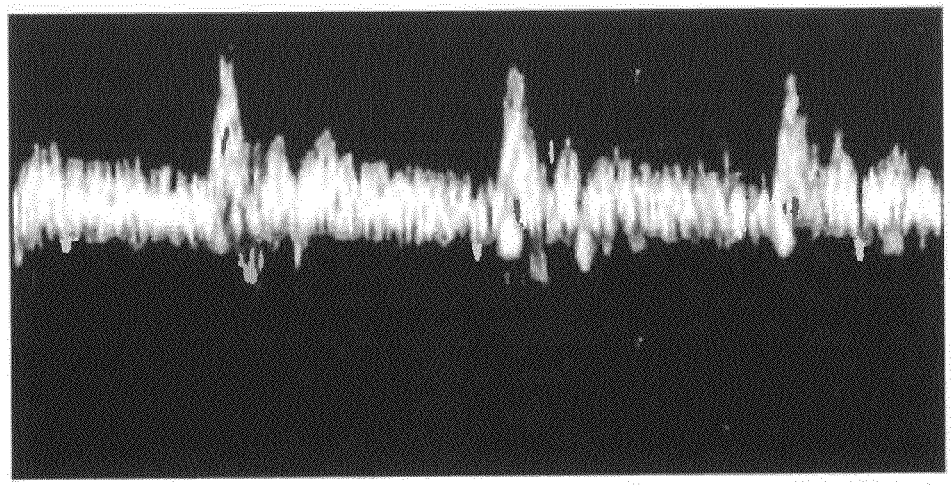
FIG. 6B shows a noise-removed spectrum image.
Figure 6C:
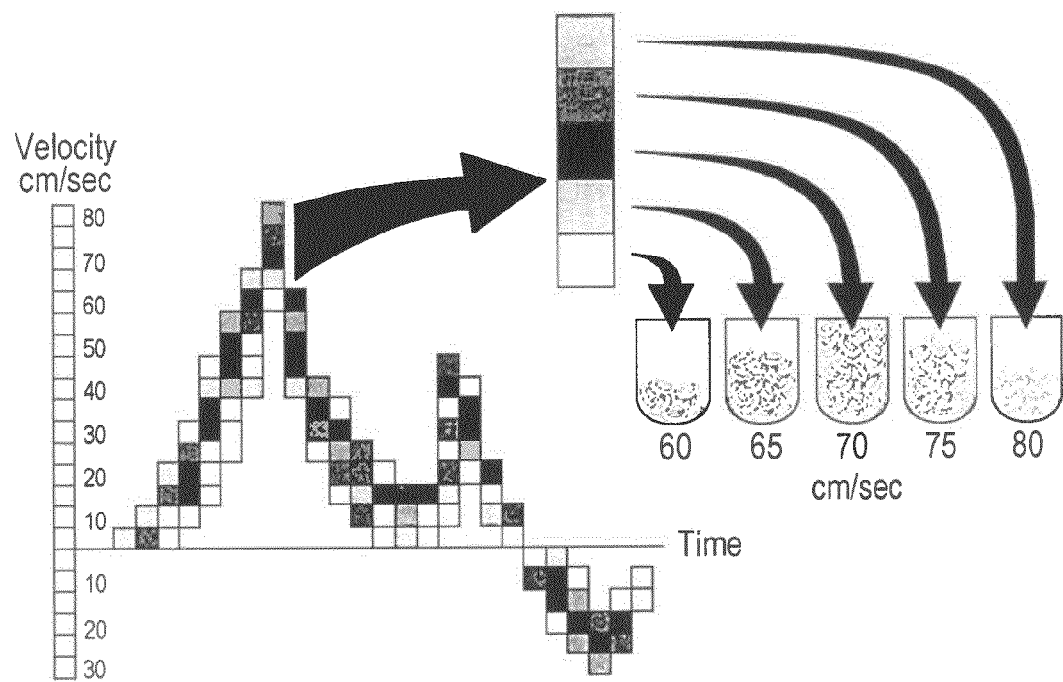
FIG. 6C is a graph of velocity versus time, wherein a frequency component at a specific time and velocity is represented by gray shading.
Figure 7:
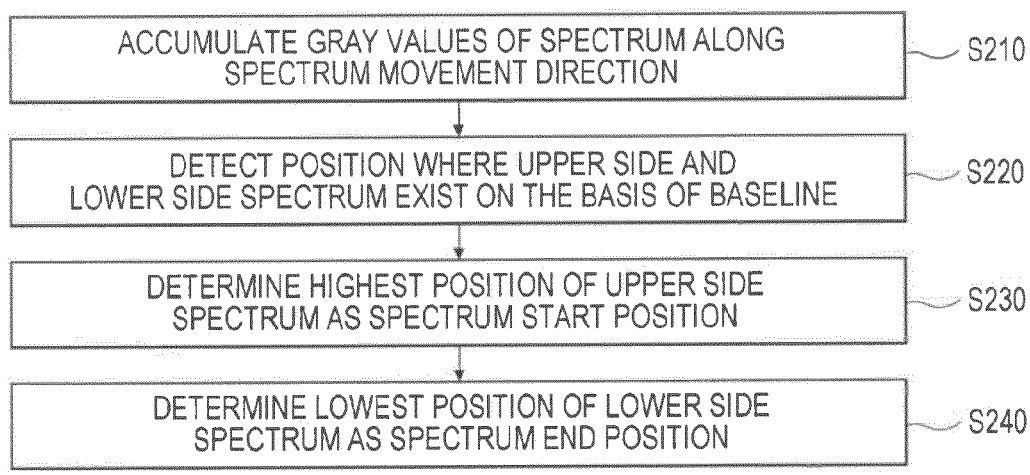
FIG. 7 is a flowchart showing the process of determining the range of a spectrum in a noise-removed spectrum image.

As shown in FIG. 5, the image processor 130 produces a spectrum image based on the spectrum signals (S110). Then, the image processor 130 divides the produced spectrum image into a number of sections (S120). Each of the sections may or may not overlap with neighboring sections. Thereafter, for each of the sections, the image processor 130 calculates the average intensity of pixels, the intensities of which are greater than a specific magnitude (S130). Next, the image processor 130 compares the average intensities calculated for the respective sections so as to detect a section with the smallest average intensity (S140). The section having the smallest average intensity is assumed to contain only the noise and not the spectrum. The image processor 130 then detects the maximum intensity of the noise by analyzing a histogram of the section having the smallest average intensity (S150). The image processor 130 then determines the detected maximum intensity of the noise as the threshold for discriminating between the noise and the spectrum (S160). The image processor 130 removes the noise from the spectrum image based on the determined threshold (S170). That is, the image processor 130 removes the noise from the noise-containing spectrum image (as shown in FIG. 6A) based on the determined threshold, thereby providing a spectrum image containing only the spectrum (as shown in FIG. 6B). FIG. 6C represents FIG. 6B in more detail, wherein a frequency component at a specific time and velocity is represented by a gray scale variation.

After completing step S100, the image processor 130 determines a range covering the spectrum in the noise-removed spectrum image (S200). Step S200 will be described in more detail with reference to FIGS. 7 and 8.

Figure 8:
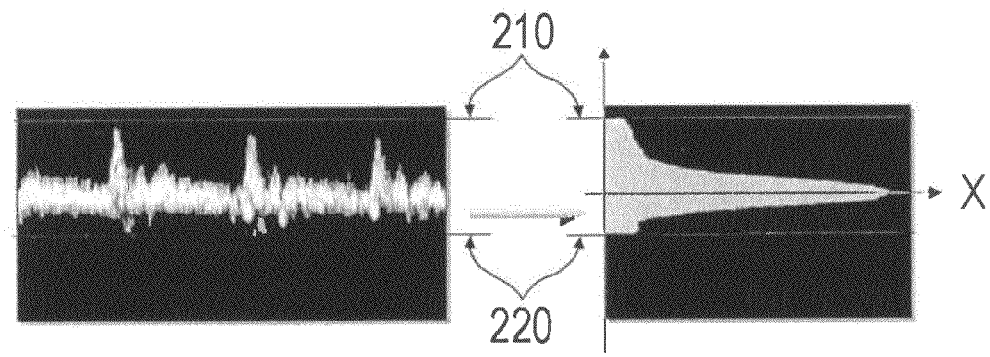
FIG. 8 shows the accumulation of gray values of a spectrum along a horizontal axis, as well as a spectrum start position and a spectrum end position, in accordance with one embodiment of the present invention.

The image processor 130 accumulates gray values of the spectrum in the noise-removed spectrum image along the spectrum movement direction (direction of X-axis), as shown in FIG. 8 (S210). The image processor 130 then detects the range including upper side and lower side spectrums from a baseline (S220). The image processor 130 determines the highest position (or velocity) of the upper side spectrum from the baseline as a spectrum start position 210 (S230). Further, the image processor 130 determines the lowest position (or velocity) of the lower side spectrum from the baseline as a spectrum end position 220 (S240).

In an alternative embodiment, the image processor 130 may detect the velocities of the upper side and lower side spectrums from the baseline. It can then determine the highest spectrum velocity in the upper side spectrum as the spectrum start position, while further determining the highest spectrum velocity in the lower side spectrum as the spectrum end position.

Figure 9A:
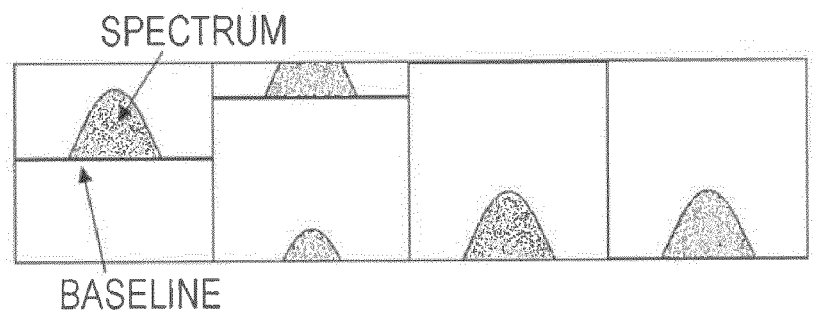
FIGS. 9A to 9C show the spectrum models in accordance with one embodiment of the present invention.
Figure 9B:
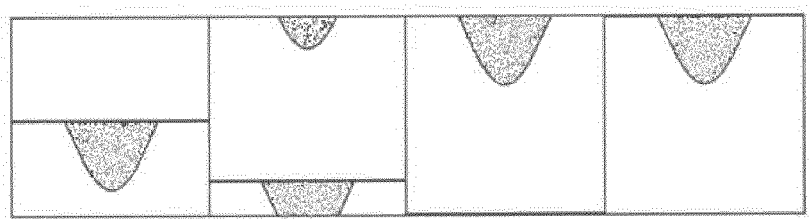
Figure 9C:
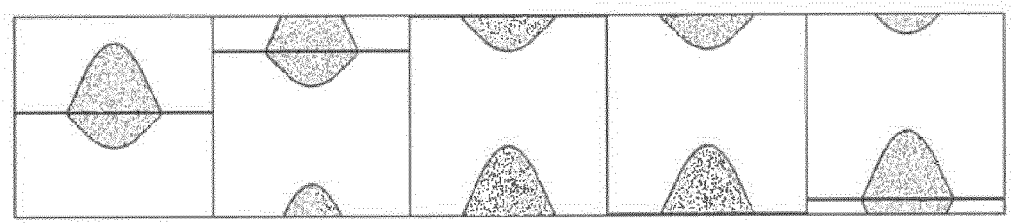

After completing step S200, the image processor 130 checks whether an aliasing exists in the spectrum image or not. In case the spectrum image contains the aliasing, the image processor 130 shifts the baseline of the spectrum image to convert the aliasing-containing spectrum image into an aliasing-removed spectrum image (S300). Whether an aliasing exists or not is determined based on the spectrum models, which represent the spectrum types. More specifically, the spectrum models may include the spectrum types wherein a spectrum resides in the upper side of the baseline (FIG. 9A), the spectrum types wherein a spectrum resides in the lower side of the baseline (FIG. 9B), and the spectrum types wherein a spectrum resides in both the upper side and lower side of the baseline (FIG. 9C). Step S300 will be described in more detail with reference to FIGS. 10, 11A and 11B.

Figure 10:
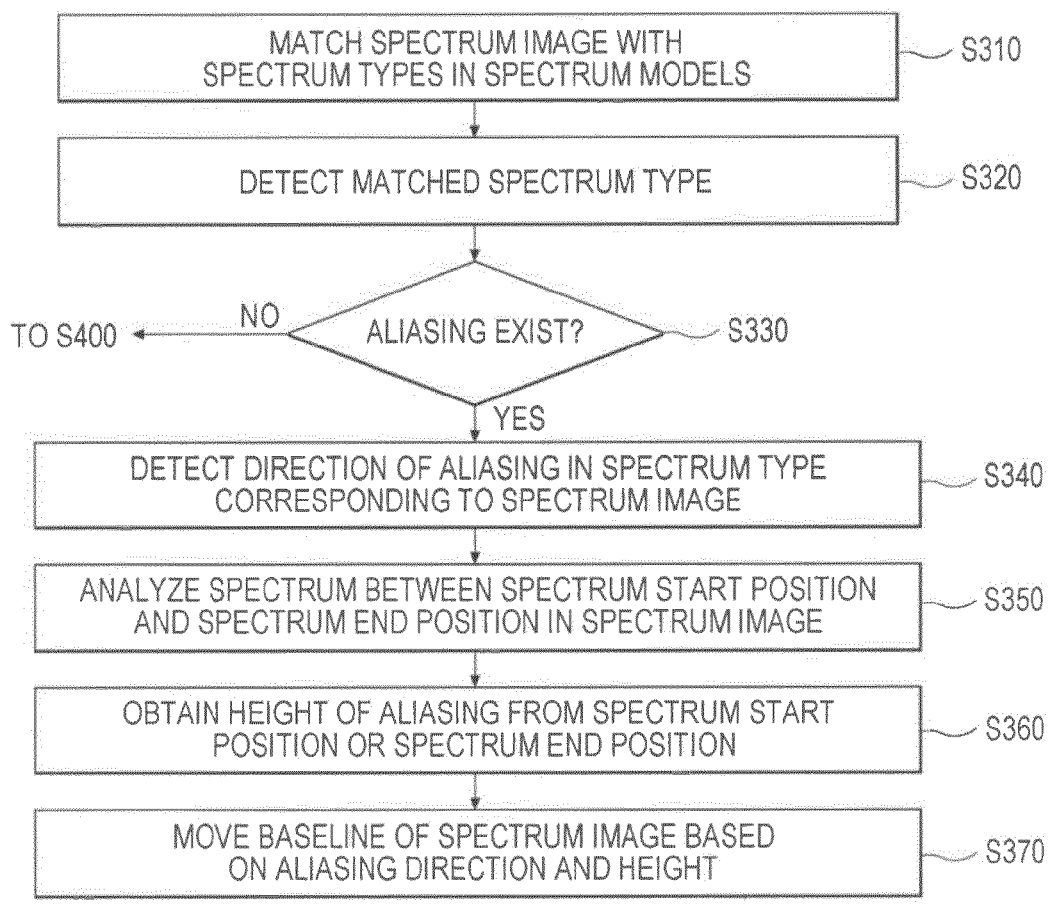
FIG. 10 is a flowchart showing the process of converting an aliasing-containing spectrum image into an aliasing-removed spectrum image by shifting a baseline based on its spectrum model.
Figure 11A:
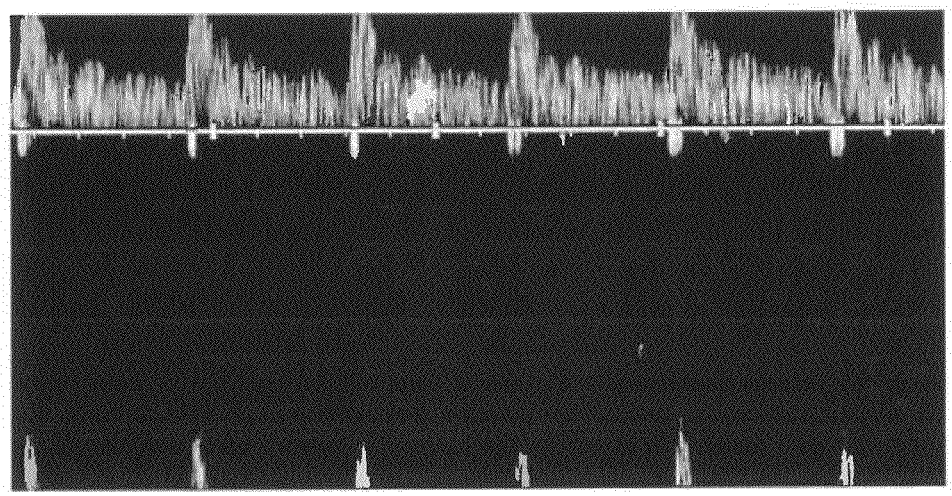
FIG. 11A shows an aliasing-containing spectrum image.
Figure 11B:
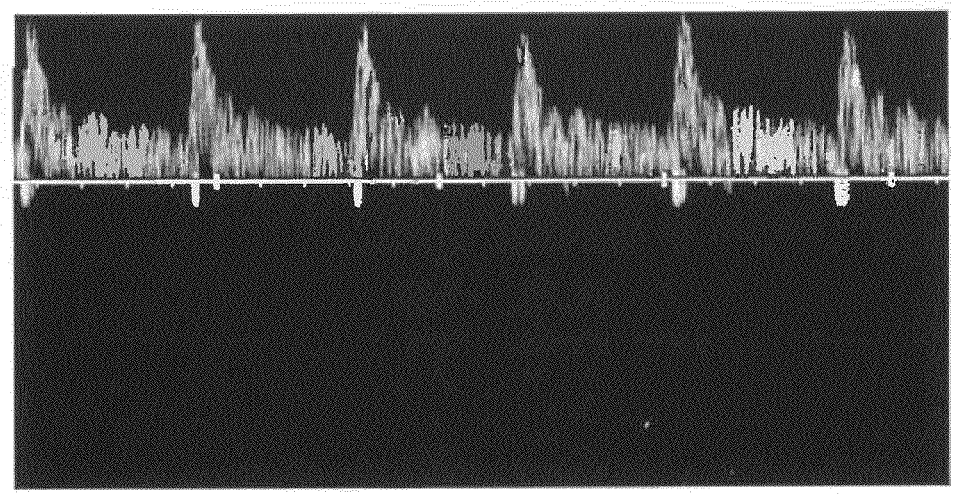
FIG. 11B shows a spectrum image with a baseline shifted in accordance with one embodiment of the present invention.

As shown in FIG. 10, the image processor 130 matches the spectrum image with the spectrum types in the spectrum models (S310). By doing so, the image processor 130 detects a spectrum type that corresponds to the spectrum image (S320). For example, by matching the spectrum image (as shown in FIG. 11A) with the spectrum types (as shown in FIGS. 9A to 9C), the image processor 130 detects the second spectrum type in FIG. 9C as the spectrum type corresponding to the spectrum image. Thereafter, the image processor 130 checks whether the detected spectrum type contains the aliasing or not (S330). In case the detected spectrum type does not contain the aliasing, it proceeds to step S400. In case the aliasing exists in the detected spectrum type, the image processor 130 detects the direction of the aliasing in the spectrum type and determines the direction in which the baseline should be shifted based on the detected direction (S340). For example, the image processor 130 determines that the spectrum type corresponding to the spectrum image shown in FIG. 11A (second spectrum type in FIG. 9C) contains the aliasing in the upper side spectrum, and further determines that the baseline should be shifted downward. Moreover, the image processor 130 analyzes the spectrum between the spectrum start position and the spectrum end position in the spectrum image (S350) so as to obtain the height of the aliasing from the spectrum start position or the spectrum end position (S360). Then, the image processor 130 shifts the baseline of the spectrum image based on the aliasing direction detected at step S340 and the aliasing height obtained at step S360 in order to remove the aliasing, as shown in FIG. 11B (S370).

After completing step S300, the image processor 130 determines a contour tracing direction of the spectrum image and performs contour tracing in the determined direction (S400). Step S400 will be described in more detail with reference to FIG. 12.

Figure 12:
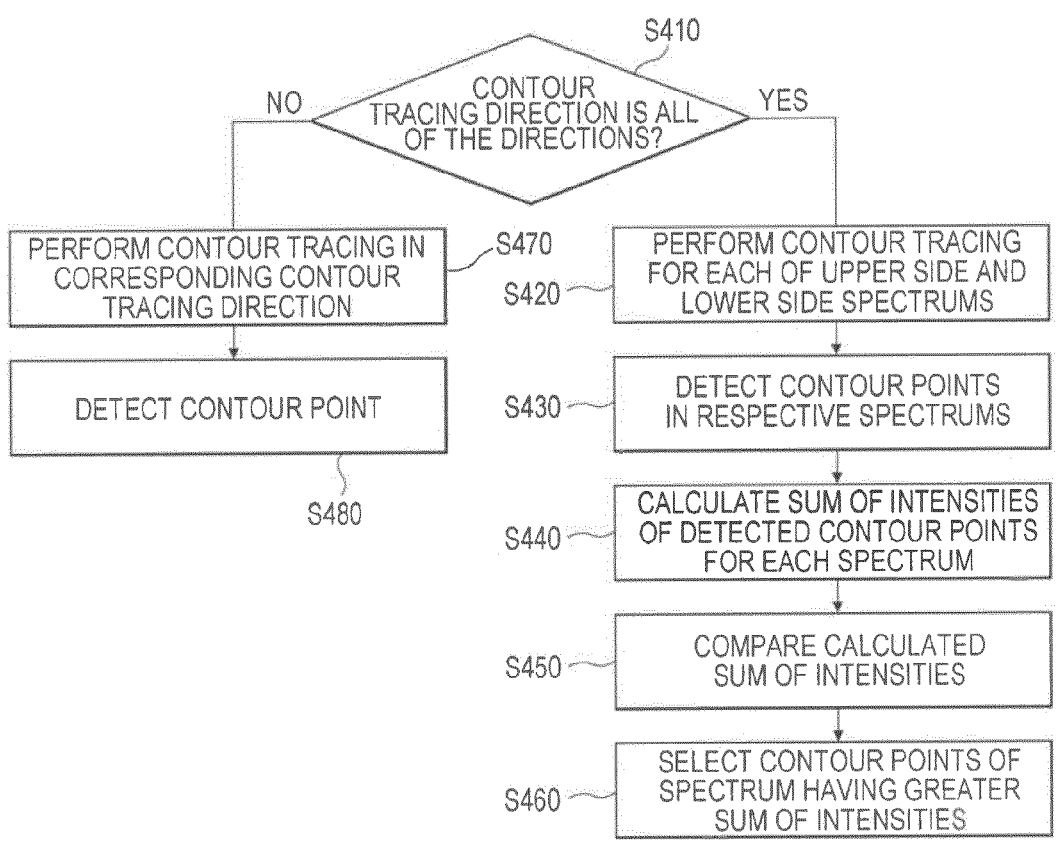
FIG. 12 is a flowchart showing the process of determining a contour tracing direction for a spectrum image and performing contour tracing in the determined direction.

As shown in FIG. 12, the image processor 130 checks whether the contour tracing direction selected by an operator is all of the directions or an up/down direction (S410). If the up direction is selected, the contour tracing is performed for the upper side spectrum above the baseline. If the down direction is selected, the contour tracing is performed for the lower side spectrum below the baseline. If all the directions are selected, the contour tracing is performed for both the upper side and lower side spectrums.

In case it is determined that the contour tracing direction is all of the directions at step 410, the contour tracing is performed for each of the upper side and lower side spectrums (S420) to detect contour points in the respective spectrums (S430). Next, for each of the upper side and lower side spectrums, the image processor 130 calculates the sum of the intensities of the detected contour points (S440). The intensity refers to the sum of frequency components with regard to specific velocities and time points in a spectrum. For example, as the contour point A in FIG. 6C includes the information of frequency components of various velocities (60 cm/sec, 65 cm/sec, 70 cm/sec, 75 cm/sec and 80 cm/sec), the image processor 130 calculates the intensity of the contour point A by summing up the velocity magnitude multiplied by the frequency components. The image processor 130 compares the calculated sum of intensities between the upper side spectrum and the lower side spectrum (S450) to select the contour points of the spectrum having the greater sum of intensities (S460).

On the other hand, in case it is determined that the contour tracing direction is the up or down direction at step 410, the image processor 130 performs the contour tracing in the corresponding contour tracing direction (S470) to detect contour points (S480).

After completing step S400, the image processor 130 performs mean contour tracing to detect mean contour points (S500). The intensity at each of the mean contour points is half the intensity at the corresponding contour point. Step S500 will be described in more detail with reference to FIGS. 13 and 14.

Figure 13:
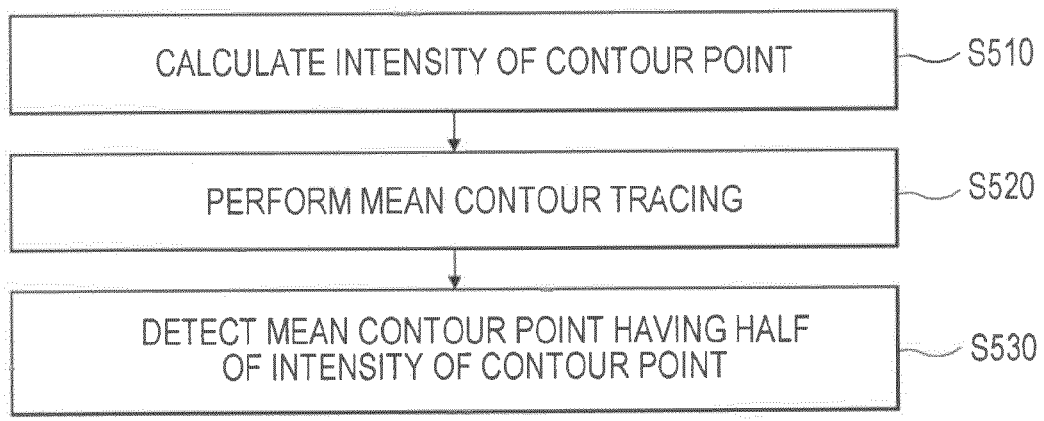
FIG. 13 is a flowchart showing the process of performing mean contour tracing for a spectrum image.
Figure 14:
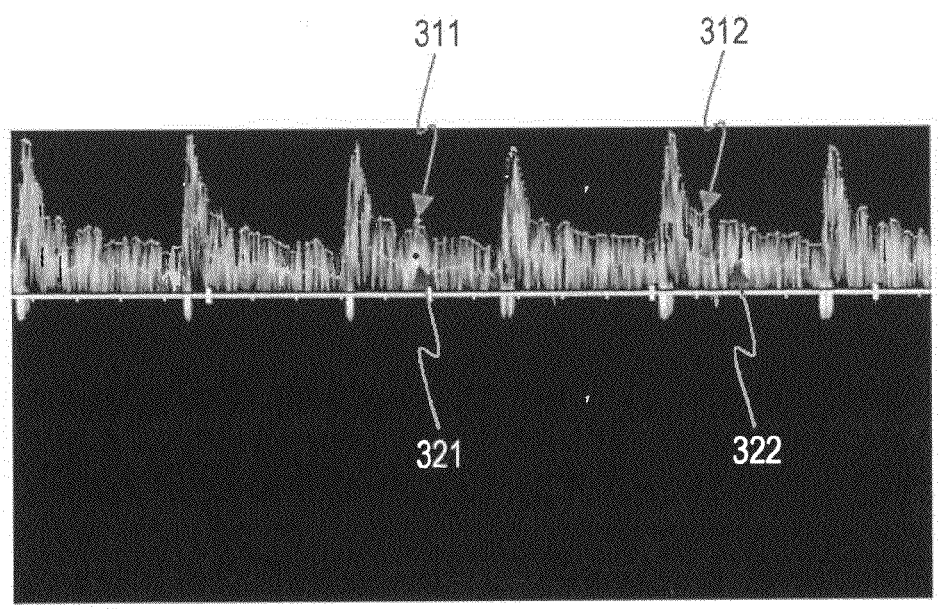
FIG. 14 shows the contour points, mean contour points, result of contour tracing and result of mean contour tracing, which are obtained in accordance with one embodiment of the present invention.

As shown in FIG. 13, the image processor 130 calculates the intensities of the contour points (S510). The image processor 130 then performs mean contour tracing (S520) to detect mean contour points (S530). For example, as shown in FIG. 14, the image processor 130 performs the mean contour tracing to detect a mean contour point 321 for a contour point 311 (the former having half the intensity of the latter) when the baseline is adopted as the reference. In FIG. 14, reference numeral 312 represents the result of the contour tracing, while reference numeral 322 represents the result of the mean contour tracing.

After completing step S500, the image processor 130 determines a peak tracing direction of the spectrum image (S600). Step S600 will be described in more detail with reference to FIG. 15.

Figure 15:
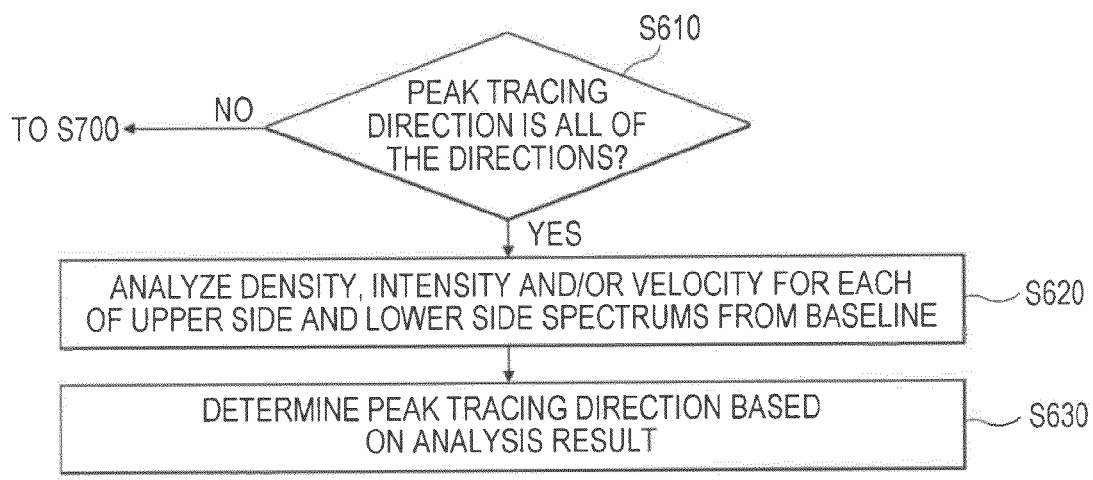
FIG. 15 is a flowchart showing the process of determining the peak tracing direction of a spectrum image.

As shown in FIG. 15, the image processor 130 checks whether the peak tracing direction selected by an operator is all of the directions or an up/down direction (S610). If the selected peak tracing direction is all of the directions, then the image processor 130 analyzes the density, intensity and/or velocity for each of the upper side and lower side spectrums from the baseline (S620). The image processor 130 determines the peak tracing direction based on the result of the analysis (S630). Preferably, the image processor 130 determines the peak tracing direction to correspond to the spectrum having the higher density, intensity and/or velocity (between the upper side spectrum and the lower side spectrum). However, if the peak tracing direction is the up/down direction, then it proceeds to step S700.

After completing step S600, the image processor 130 checks whether the peak tracing, which is performed to detect peaks, is 1-peak tracing or 2-peak tracing (S700). The 1-peak tracing is generally used for a spectrum image having one peak per cycle (e.g., a spectrum image obtained far from the heart) to detect peaks and peak start positions. The 2-peak tracing is generally used for a spectrum image having two peaks per cycle (e.g., a spectrum image obtained near the heart) to detect two peaks for each cycle.

In case it is determined that the peak tracing is the 1-peak tracing at step S700, the image processor 130 performs the 1-peak tracing in the peak tracing direction (S800). Step S800 will be described in more detail with reference to FIGS. 16 to 19.

Figure 16:
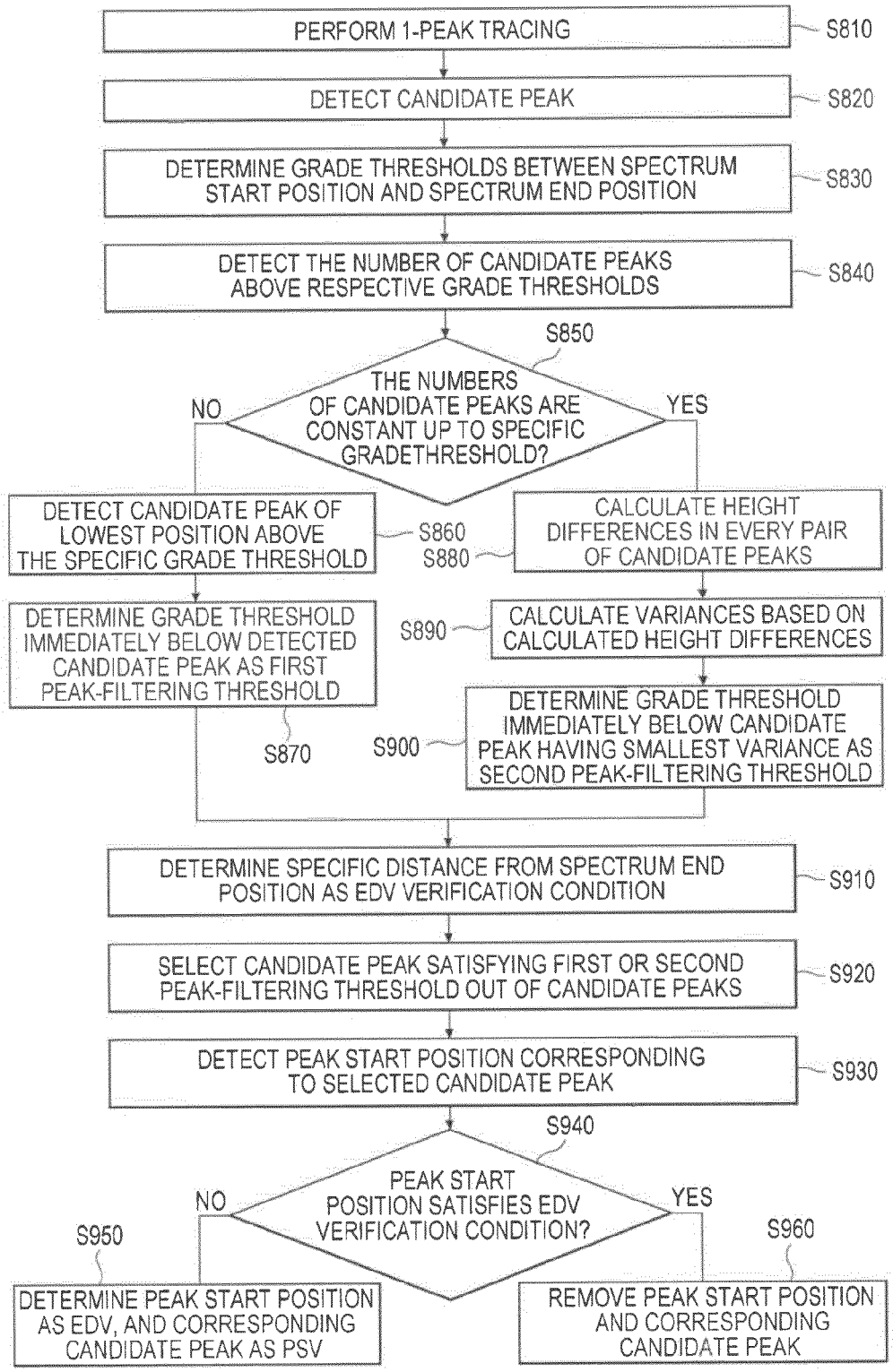
FIG. 16 is a flowchart showing the process of performing 1-peak tracing in a peak tracing direction of a spectrum image.
Figure 17A:
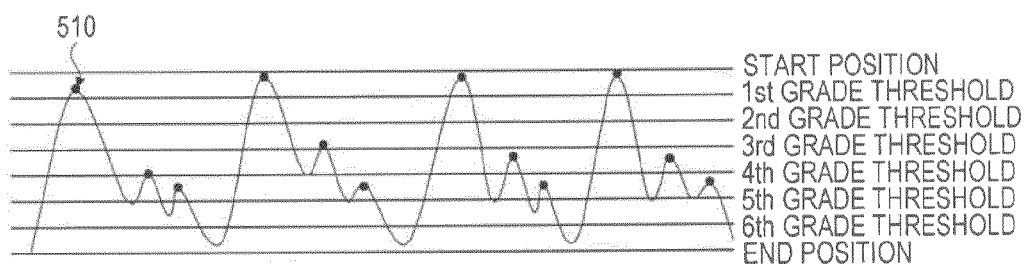
FIG. 17A shows an example wherein the number of peaks, which are above their respective grade thresholds, are constant up to a specific grade threshold in accordance with one embodiment of the present invention.
Figure 17B:
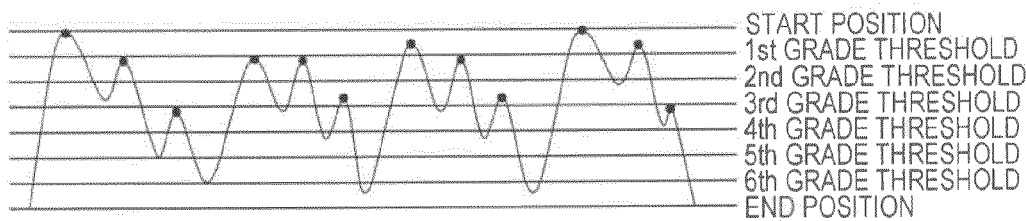
FIG. 17B shows an example wherein the number of peaks, which are above their respective grade thresholds, are not constant in accordance with one embodiment of the present invention.
Figure 18:
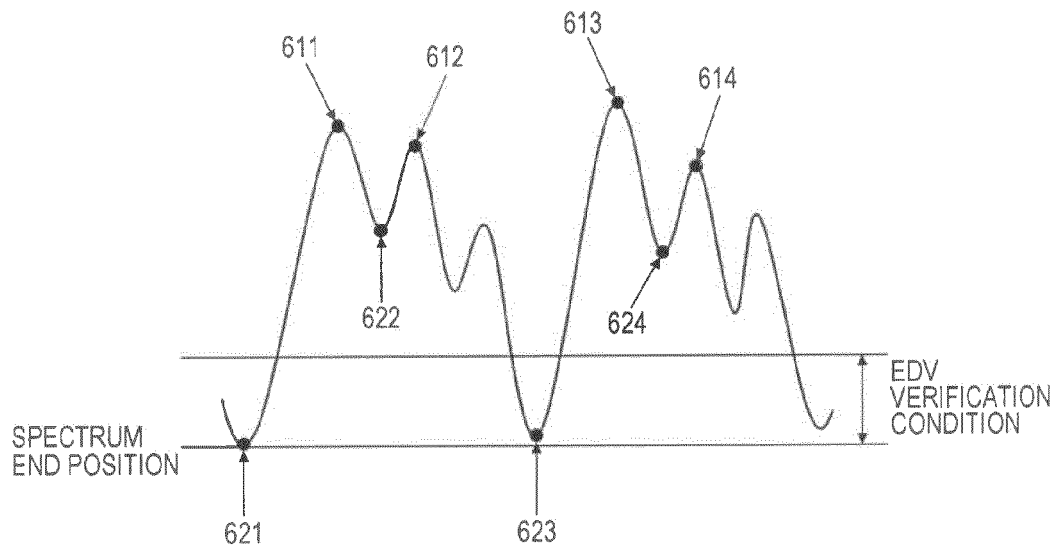
FIG. 18 shows the end diastolic velocity (EDV) verification condition, EDVs and peak systolic velocities (PSVs)

As shown in FIG. 16, the image processor 130 performs the 1-peak tracing (S810) to detect candidate peaks (S820). The candidate peaks include actual peaks corresponding to the peak systolic velocity (PSV) and quasi-peaks, which are similar to the actual peaks. The image processor 130 determines grade thresholds, which divide the range between the spectrum start position and the spectrum end position into several grades of the peak velocity (S830). Then, for each of the grade thresholds starting from the spectrum start position (or the spectrum end position), the image processor 130 detects the number of candidate peaks higher than the corresponding grade threshold (S840). For illustration, the image processor 130 may determine the grade thresholds between the spectrum start position and the spectrum end position (as shown in FIG. 17A or FIG. 17B) and then detect the number of candidate peaks residing above each of the grade thresholds. In FIG. 17A, the number of candidates peaks above the first grade threshold is four and above the second grade threshold is four. Further, the number of candidate peaks above the third grade threshold is five and above the fourth grade threshold is eight.

The image processor 130 checks whether or not the number of candidate peaks above the respective grade thresholds are constantly repeated up to a specific grade threshold (S850). If it is determined that the number of candidate peaks above the grade thresholds are constantly repeated up to the specific grade threshold at step S850, then the image processor 130 detects the candidate peak of the lowest position among the candidate peaks above the specific grade threshold (S860). Then, the image processor 130 determines as a first peak-filtering threshold, which is used for filtering the candidate peaks, the grade threshold immediately below the detected candidate peak of the lowest position (S870). For illustration, in case of FIG. 17A, the image processor 130 determines that the number of candidate peaks are constantly repeated at four up to the second grade threshold. The image processor 130 then determines the first grade threshold located immediately below the candidate peak 150, which has the lowest position among the candidate peaks above the second grade threshold, as the first peak-filtering threshold. In another embodiment, the image processor 130 may determine as the first peak-filtering threshold the position of the candidate peak of the lowest position among the candidate peaks above the specific grade threshold.

On the other hand, at step S850, it may be determined that the number of candidate peaks above the respective grade thresholds are not constantly repeated up to any specific grade threshold. For example, in FIG. 17B, the number of candidate peaks are as follows: above the first grade threshold is four; above the second grade threshold is eight; above the third grade threshold is ten; and above the fourth grade threshold is twelve. In such a case, the image processor 130 calculates the height differences in every pair of the candidate peaks (S880). Then, the image processor 130 calculates the variance for each of the candidate peaks based on the calculated height differences (S890). The image processor 130 then detects the candidate peak having the smallest variance and determines as a second peak-filtering threshold, which is used for filtering the candidate peaks, the grade threshold immediately below the detected candidate peak (S900).

Based on the distance between the spectrum start position and the spectrum end position, the image processor 130 determines the end diastolic velocity (EDV) verification condition, which is used for verifying the peak start positions, to be a position corresponding to a specific distance (preferably 30% of the distance between the spectrum start position and the spectrum end position) from the spectrum end position (S910). The image processor 130 selects the candidate peaks satisfying the first or second peak-filtering threshold out of all the candidate peaks (S920). Then, the image processor 130 detects the peak start positions corresponding to the selected candidate peaks (S930). The image processor 130 checks whether each of the detected peak start positions satisfies the EDV verification condition determined at step S910 or not (S940).

If the peak start position is determined to satisfy the EDV verification condition at step S940, then the peak start position is determined as an EDV and the candidate peak corresponding thereto is determined as a PSV (S950). For example, in FIG. 18, the image processor 130 detects the peak start positions 621, 622, 623 and 624 for the respective candidate peaks 611, 612, 613 and 614 that satisfy the first or second peak-filtering threshold. Then, the image processor 130 selects the peak start positions 621 and 623, which satisfy the EDV verification condition, out of the detected peak start positions 621, 622, 623 and 624. The image processor 130 determines the peak start positions 621 and 623 as EDVs and determines the candidate peaks 611 and 613 corresponding to the peak start positions 621 and 623 as PSVs.

Figure 19:
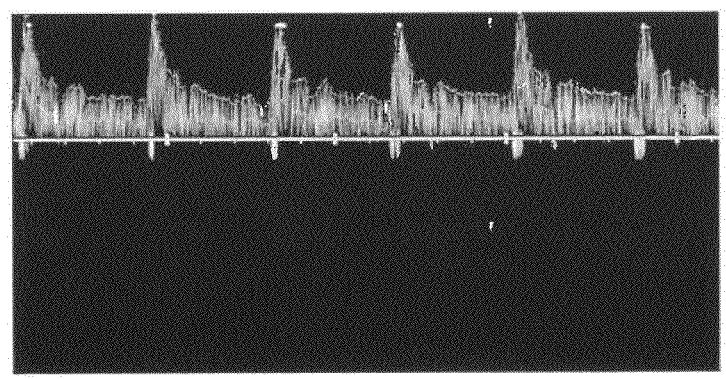
FIG. 19 shows the result of 1-peak tracing in accordance with one embodiment of the present invention.

On the other hand, if the peak start position is determined not to satisfy the EDV verification condition at step S940, then the peak start position and the candidate peak corresponding thereto are removed (S970). For example, in FIG. 18, the peak start positions 622 and 624 and the candidate peaks 612 and 614 corresponding thereto are removed. By determining EDVs and PSVs along the aforementioned steps, the image processor 130 can automatically detect individual cycles in the spectrum image. The image processor 130 then outputs the result of the 1-peak tracing, as shown in FIG. 19.

However, if it is determined that the peak tracing is 2-peak tracing at step S700, then the image processor 130 performs the 2-peak tracing in the peak tracing direction (S1000). Step S1000 will be described in more detail with reference to FIGS. 20 and 21.

Figure 20:
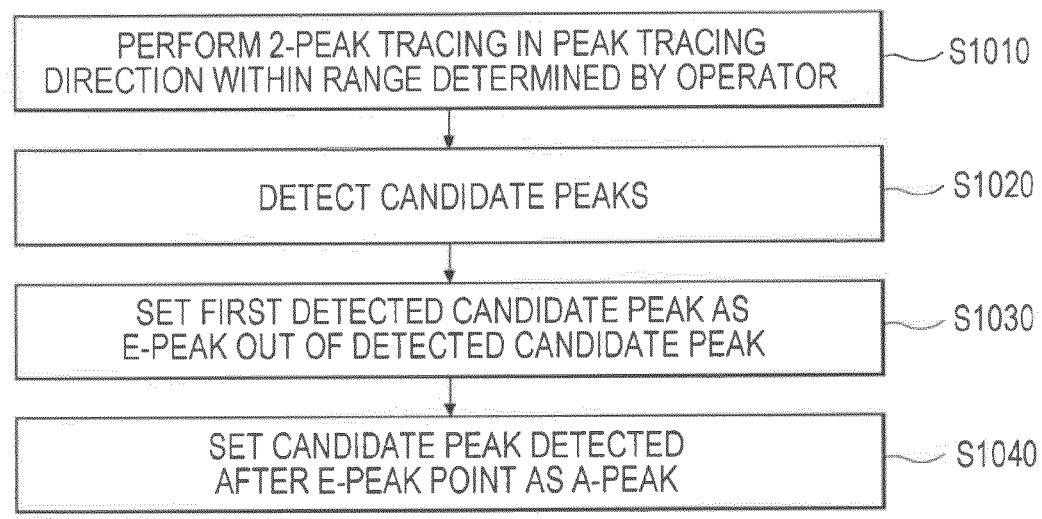
FIG. 20 is a flowchart showing the process of performing 2-peak tracing in a peak tracing direction of a spectrum image.
Figure 21:
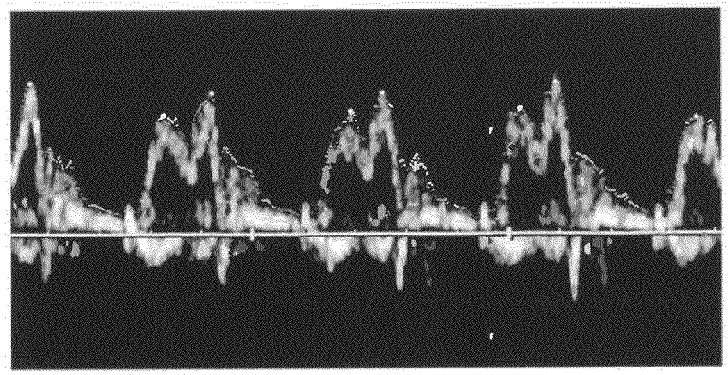
FIG. 21 shows the result of 2-peak tracing in accordance with one embodiment of the present invention.

As shown in FIG. 20, the image processor 130 performs the 2-peak tracing in the peak tracing direction within a range determined by an operator (S1010) so as to detect candidate peaks (S1020). Next, among the detected candidate peaks, the image processor 130 determines a first detected candidate peak as an E-peak (end of rapid filling peak) (S1030) and further determines a candidate peak detected after the E-peak as an A-peak (atrial contraction peak) (S1040). Thereafter, the image processor 130 outputs the result of the 2-peak tracing as shown in FIG. 21.

Figure 22:
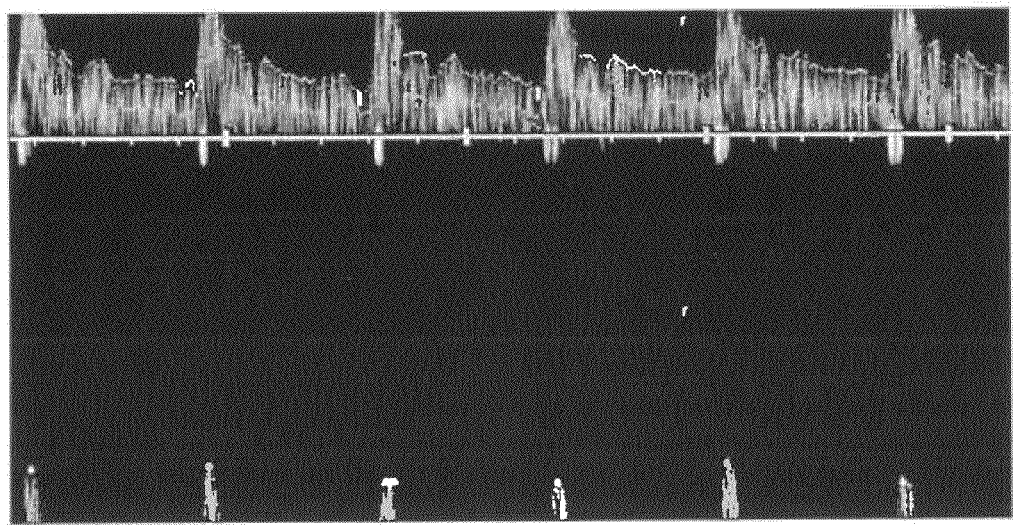
FIG. 22 shows a spectrum image with a baseline shifted back to an original position after completing contour tracing and peak tracing in accordance with one embodiment of the present invention.

After completing step S800 or S1000, in case the baseline of the spectrum image was shifted at step S340, the image processor 130 shifts the baseline of the spectrum image back to the original position (i.e., the position before the shift at step S340), as shown in FIG. 22 (S1100). Step S1100 is carried out only for a spectrum image determined to contain an aliasing at step S330 and the baseline of which was shifted at step S340. Step S1100 is not carried out for a spectrum image that was determined not to contain an aliasing at step S330. Thereafter, the image processor 130 stores the processing result in the memory unit 140 and/or displays the same on the display unit 150 (S1200).

As discussed above, the present invention can remove the noise from a noise-containing spectrum image, as well as being able to remove the aliasing from an aliasing-containing spectrum image by automatically shifting the baseline. As such, the present invention can provide accurate contour tracing and accurate peak tracing.

While the present invention has been shown and described with respect to a preferred embodiment, those skilled in the art will recognize that various changes and modifications may be made without departing from the spirit and scope of the invention as defined in the appended claims.

What is claimed is:

1. A method of processing an ultrasound spectrum image, comprising the steps of:
   forming a spectrum image based on ultrasound data;
   dividing the spectrum image into a number of sections;
   calculating an average intensity of pixels in each of the sections;
   comparing the average intensities calculated for the sections to select a section having a smallest average intensity;
   analyzing a histogram of the section having the smallest average intensity to detect a maximum intensity in the histogram;
   determining the detected maximum intensity as a threshold for removing a noise from the spectrum image; and
   removing the noise from the spectrum image based on the determined threshold.

2. A method of processing an ultrasound spectrum image, comprising the steps of:
   forming a spectrum image based on ultrasound data;
   matching the spectrum image with one or more spectrum models representing specific spectrum types to check whether or not the spectrum image contains an aliasing;
   detecting a direction and a magnitude of the aliasing, if the spectrum image contains the aliasing, based on the matched spectrum model; and
   shifting a baseline of the spectrum image based on the detected direction and magnitude of the aliasing to remove the aliasing.

3. A method of processing an ultrasound spectrum image, comprising the steps of:
   (a) forming a spectrum image based on ultrasound data;
   (b) checking whether a peak tracing for detecting peaks in the spectrum image is 1-peak tracing for detecting one peak per cycle or 2-peak tracing for detecting two peaks per cycle;
   (c) performing, when the peak tracing is the 1-peak tracing, the 1-peak tracing on the spectrum image to detect candidate peaks including actual peaks and quasi peaks and selecting the actual peaks out of the candidate peaks, wherein the selecting the actual peaks comprises:
      (c21) determining a first threshold for filtering the candidate peaks;
      (c22) selecting candidate peaks satisfying the first threshold out of the candidate peaks;
      (c23) detecting peak start positions for the selected candidate peaks;
      (c24) determining a specific distance from a lowest position of a spectrum in the spectrum image as a second threshold for verifying the peak start positions; and
      (c25) selecting peak start positions satisfying the second threshold out of the peak start positions and selecting the candidate peaks corresponding to the selected peak start positions as the actual peaks out of the candidate peaks selected in the step (c23); and
   (d) performing, when the peak tracing is the 2-peak tracing, the 2-peak tracing on the spectrum image.

4. The method of claim 3, wherein the step (c21) comprises:
   (e1) determining grade thresholds in a range of the spectrum;
   (e2) for each of the grade thresholds, calculating the number of candidate peaks above the grade threshold;
   (e3) determining the first threshold based on whether the calculated number of candidate peaks are constantly repeated up to a specific grade threshold.

5. The method of claim 4, wherein the step (e3) comprises:
   detecting, when the calculated number of candidate peaks are constantly repeated up to the specific grade threshold, a candidate peak of a lowest position among candidate peaks above the specific grade threshold; and
   determining a grade threshold immediately below the detected candidate peak as the first threshold.

6. The method of claim 4, wherein the step (e3) comprises:
calculating, when the calculated number of candidate peaks are not constantly repeated up to the specific grade threshold, height differences in every pair of the candidate peaks;
calculating a variance for each of the candidate peaks by using the calculated height differences;
detecting a candidate peak having a smallest variance; and
determining a grade threshold corresponding to the detected candidate peak as the first threshold.

7. The method of claim 3, wherein the step (c25) comprises:
(f1) checking whether or not one of the peak start positions satisfies the second threshold;
(f2) determining, when the peak start position satisfies the second threshold, the peak start position as an end diastolic velocity and determining the candidate peak corresponding to the peak start position as a peak systolic velocity;
(f3) removing, when the peak start position does not satisfy the second threshold, the peak start position and the candidate peak corresponding to the peak start position; and
(f4) repeating the steps (f1) to (f3) for each of the peak start positions.

8. The method of claim 3, wherein the step (d) comprises:
performing the 2-peak tracing to detect candidate peaks;
determining a first detected candidate peak as an E-peak; and
determining a candidate peak detected after the E-peak as an A-peak.

* * * * *